(12) United States Patent
Schmitt et al.

(10) Patent No.: US 8,765,401 B2
(45) Date of Patent: Jul. 1, 2014

(54) METHOD AND APPARATUS FOR PRODUCING HISTOLOGICAL SECTIONS WITH A MICROTOME

(75) Inventors: Christoph Schmitt, Schriesheim (DE); Volker Schneider, Sinsheim-Weiler (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1283 days.

(21) Appl. No.: 12/341,710

(22) Filed: Dec. 22, 2008

(65) Prior Publication Data

US 2009/0181422 A1    Jul. 16, 2009

(30) Foreign Application Priority Data

Jan. 10, 2008  (DE) .......................... 10 2008 000 036

(51) Int. Cl.
| | |
|---|---|
| *G01N 1/30* | (2006.01) |
| *G01N 33/48* | (2006.01) |
| *C12M 1/00* | (2006.01) |
| *B26D 7/06* | (2006.01) |
| *G01N 1/06* | (2006.01) |

(52) U.S. Cl.
CPC ............... *G01N 1/06* (2013.01); *Y10S 83/9155* (2013.01); *Y10S 83/922* (2013.01)
USPC ...... 435/40.52; 435/283.1; 83/100; 83/915.5; 83/922

(58) Field of Classification Search
CPC ............ G01N 1/06; G01N 1/36; G01N 35/04
USPC ............ 435/40.52, 283.1; 83/100, 915.5, 922
See application file for complete search history.

(56) References Cited

U.S. PATENT DOCUMENTS

| | | | |
|---|---|---|---|
| 3,191,476 A | | 6/1965 | McCormick |
| 5,746,855 A | | 5/1998 | Bolles |
| 6,699,710 B1 | * | 3/2004 | Kononen et al. ............ 435/283.1 |
| 8,025,842 B2 | | 9/2011 | Nakajima et al. |

FOREIGN PATENT DOCUMENTS

| | | |
|---|---|---|
| DE | 1 748 387 | 7/1957 |
| DE | 20 28 898 | 12/1971 |
| DE | 25 06 255 | 9/1976 |
| DE | 198 03 966 | 9/1998 |
| DE | 102 42 275 | 4/2004 |
| DE | 103 52 578 | 3/2005 |
| EP | 0 725 712 | 8/1996 |
| EP | 1 094 310 | 4/2001 |
| JP | 09101242 | 4/1997 |
| JP | 10104136 | 4/1998 |
| JP | 2002031586 | 1/2002 |
| JP | 2006052963 | 2/2006 |
| JP | 2006220559 | 8/2006 |
| WO | 93-05936 | 4/1993 |
| WO | 94/28390 | 12/1994 |

OTHER PUBLICATIONS

Fink, A new integrated concept for the improved preparation of sections of fresh or frozen tissue for light microscope histochemistry, 1986, Histochemistry, 86, 43-52.*
Ogawa et al, A simple method for studying whole sections of rice grain, 2002, Biotechnic & Histochemistry, 78, 237-242.*
Kawamoto, Use of a new adhesive film for the preparation of multipurpose fresh-frozen sections from hard tissues, whole animals, insects and plants, 2003, Arch Histol Cytol , 66, 123-143.*
Related non-published U.S. Appl. No. 12/349,321, filed Jan. 6, 2009 and assigned to Leica Biosystems Nussloch GmbH.
Related non-published U.S. Appl. No. 12/349,411, filed Jan. 6, 2009 and assigned to Leica Biosystems Nussloch GmbH.
Search Report from corresponding GB application 0821518.8 dated Feb. 27, 2009 issued by the Great Britain Patent and Trademark Office.

* cited by examiner

*Primary Examiner* — Narayan Bhat
(74) *Attorney, Agent, or Firm* — Schlee IP International, P.C.; Alexander R. Schlee

(57) ABSTRACT

A method and apparatus for producing histological sections by means of a microtome are suggested. A histological section of predefined thickness is produced with a microtome from a block comprising a tissue sample. A carrier material is applied with an application apparatus onto the block prior to before production of the histological section. To ensure that the histological sections do not roll up, and to enable improved downline processing of the histological sections as compared with a carrier material embodied in the form of an endless strip and that the carrier material is cut out prior to application to a size and/or a shape that corresponds substantially to the cross-sectional area of the block; and that the cut-out carrier material is then applied onto the block. The suggested apparatus is designed to apply the carrier material onto a histological section to be prepared by a microtome.

13 Claims, 6 Drawing Sheets

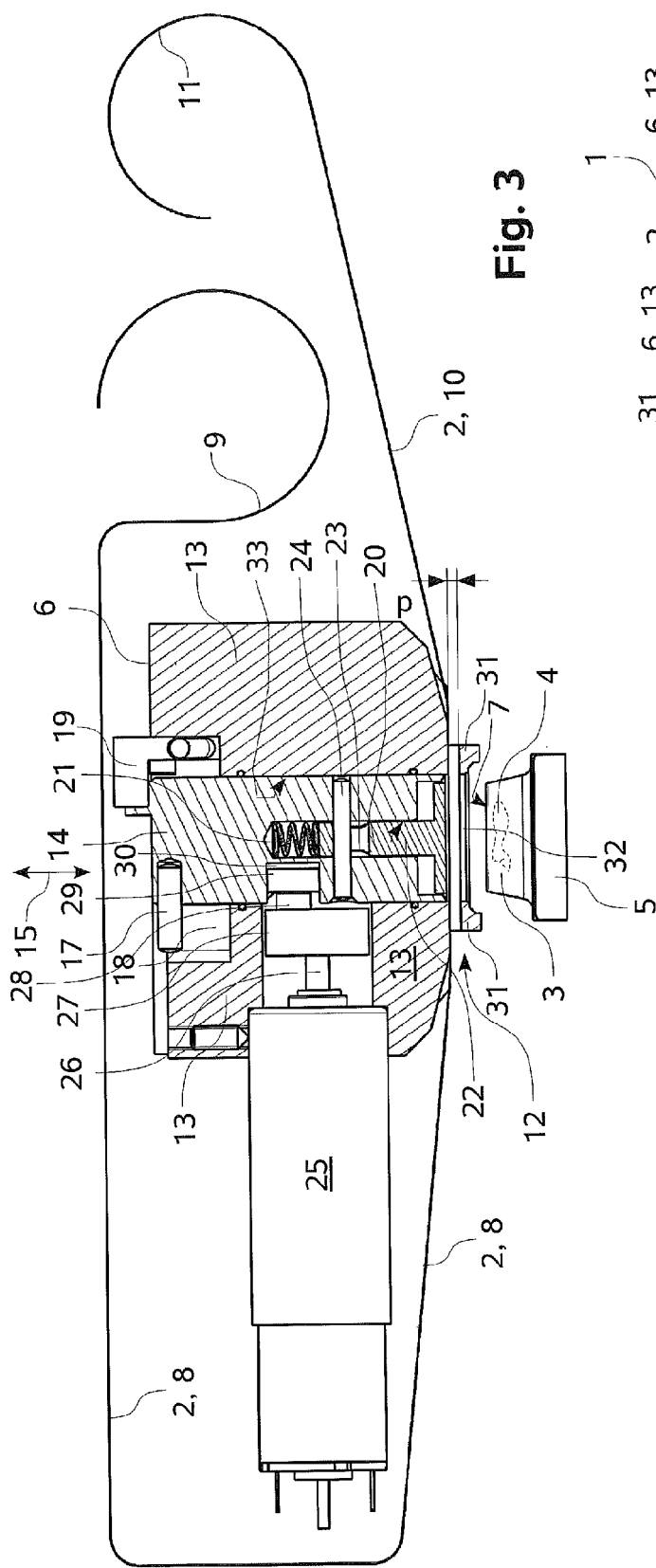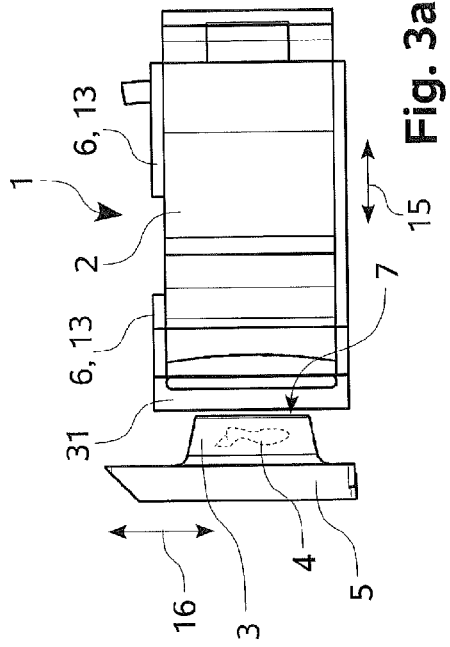

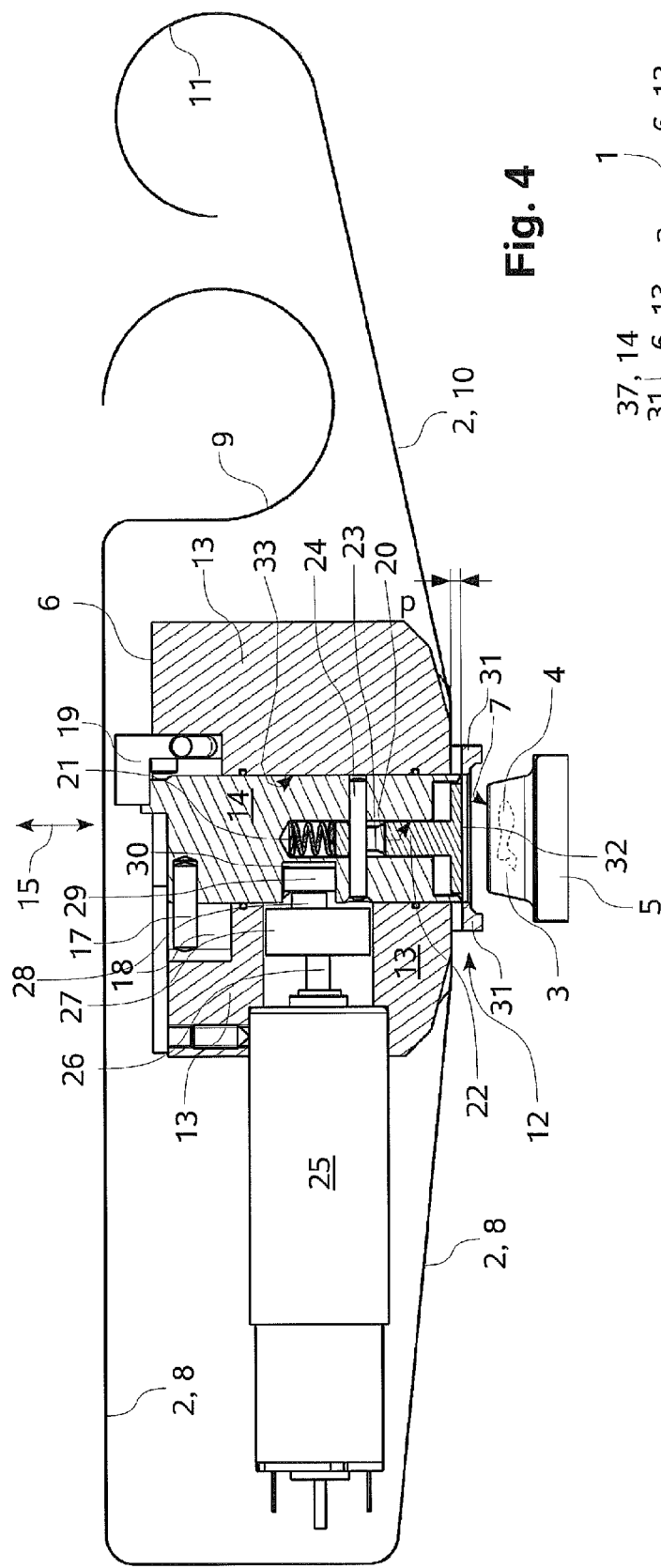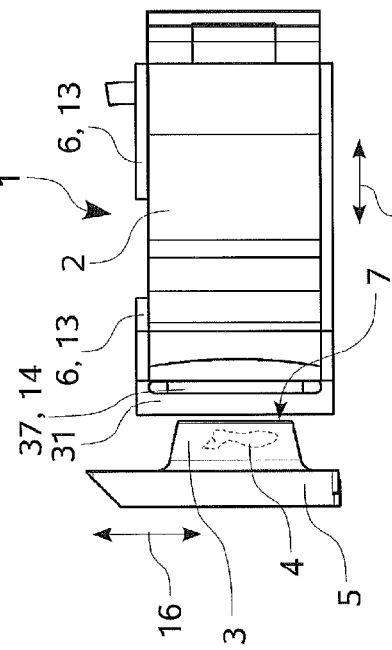

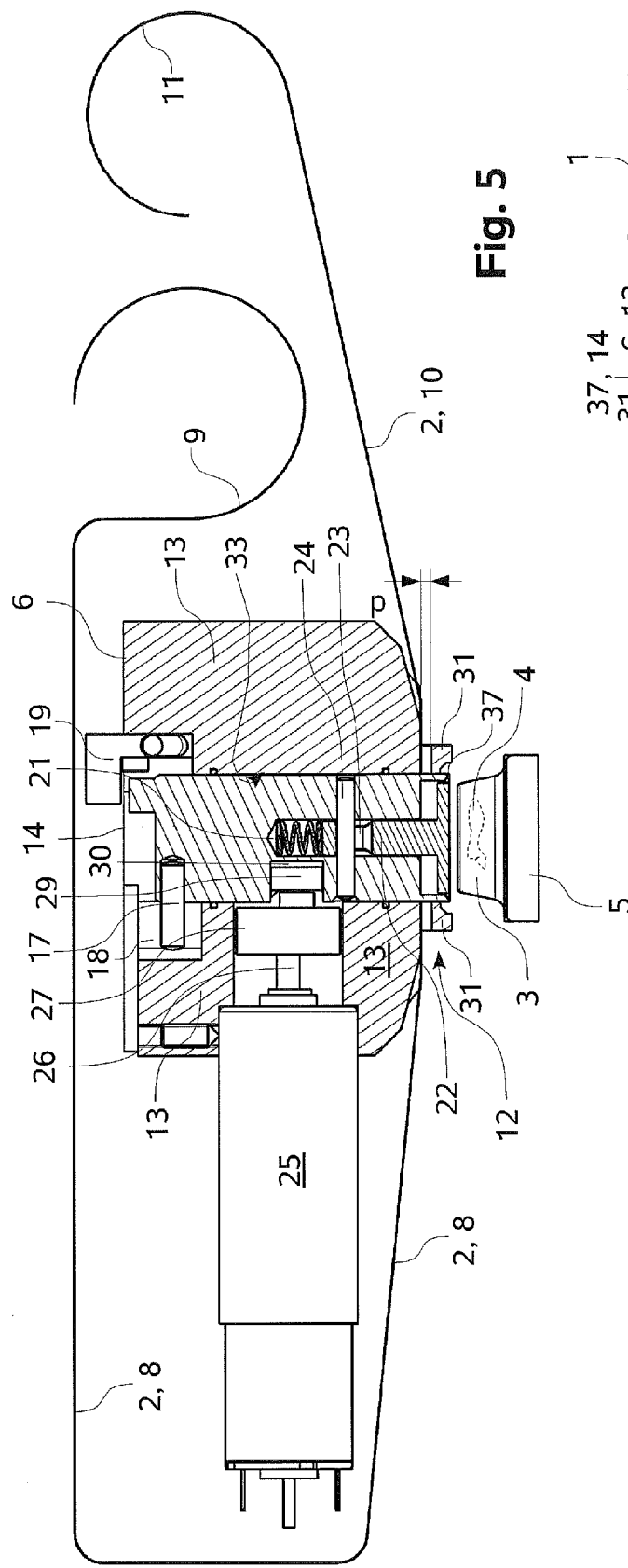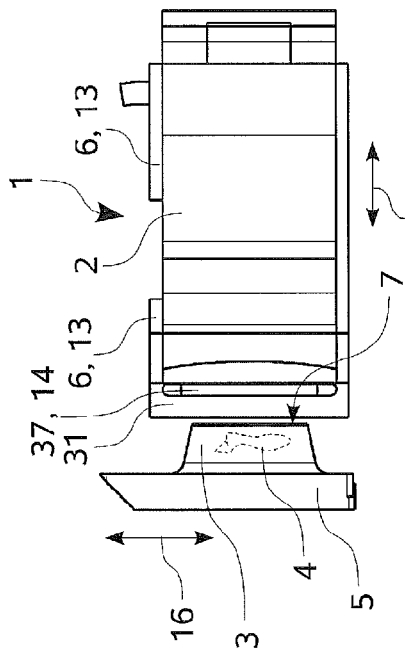

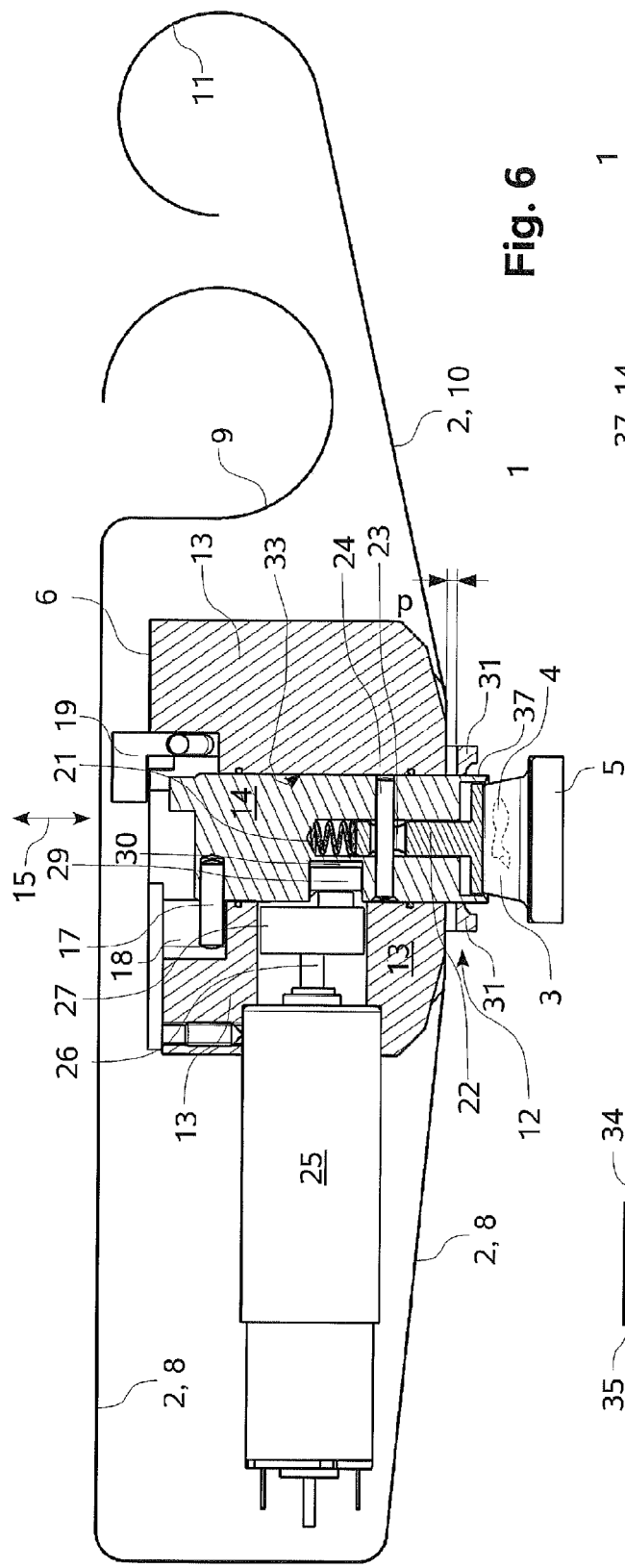
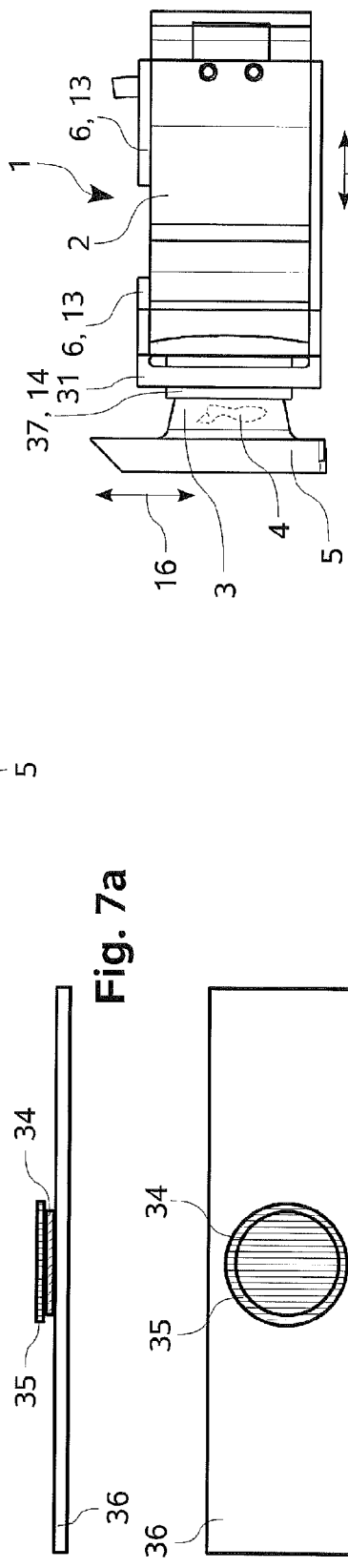
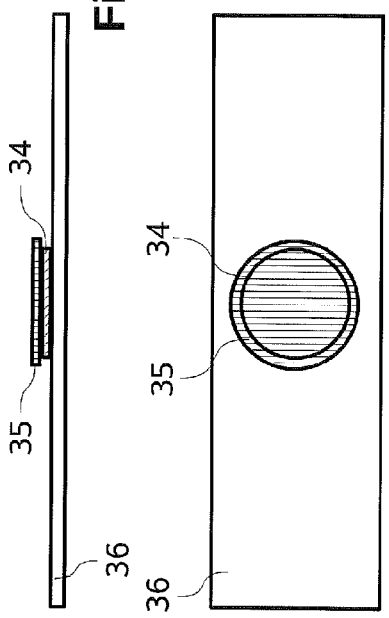
Fig. 6
Fig. 6a
Fig. 7a
Fig. 7b

METHOD AND APPARATUS FOR PRODUCING HISTOLOGICAL SECTIONS WITH A MICROTOME

CROSS-REFERENCE TO RELATED APPLICATION

This application claims the priority of the German patent application DE 102008000036.1 having a filing date of Jan. 10, 2008, the entire content of which is herewith incorporated by reference.

BACKGROUND OF THE INVENTION

The present invention relates to a method and apparatus for producing histological sections with a microtome. With a microtome, a histological section of predefinable thickness is produced from a block comprising a tissue sample. Before production of the histological section, a carrier material is applied with an application apparatus onto the block. The present invention further relates to an apparatus for applying a carrier material onto a histological section to be produced with a microtome.

A "carrier material" is to be understood for purposes of the present invention as, in particular, a flexible material of planar configuration which is such that a histological section can be mounted thereonto and adheres thereto, and can be detached again therefrom. Such a carrier material is also referred to as a "tape." The carrier material could be embodied, for example, in the form of an adhesive strip. At least one surface of the carrier material could therefore comprise a specific adhesive which is such that a histological section on the one hand adheres to the carrier material and on the other hand can be removed again from the carrier material. The carrier material could, however, also be embodied without an adhesive, so that a histological section adheres to the carrier material on the basis of adhesive forces.

Reference is made merely by way of example to U.S. Pat. No. 5,746,855, which makes known a method and an apparatus with which histological sections of predefinable sections can be produced from a block with a microtome. Immediately before production of a histological section, a carrier material embodied in the form of an endless strip is brought into contact with the block. The histological section is then produced, and adheres to the endless strip of carrier material. The endless strip is advanced so that another site on the endless strip can be brought into contact with the new surface of the block, and a further histological section can be produced. The histological sections manufactured with the method known from U.S. Pat. No. 5,746,855 are thus all present together on the endless strip of carrier material. It is advantageous in this context that the histological sections cannot roll up or, as a rule, do not exhibit corrugations or creases. It is disadvantageous in this context that downline processing with the endless strip, and in particular application of the histological sections onto specimen slides, is problematic.

BACKGROUND OF THE INVENTION

An underlying object of the present invention is therefore to describe and refine a method for producing histological sections with a microtome, in which method the histological sections do not roll up, and in which method improved downline processing is possible.

In the method according to the present invention, the carrier material is cut out, prior to application, to at least one of a size and a shape that corresponds substantially to the cross-sectional area of the block; and that the cut-out carrier material is applied onto the block.

What has been recognized according to the present invention is firstly that when histological sections are produced, the advantages associated with the carrier material can be utilized, and the disadvantages associated in particular with the carrier material of U.S. Pat. No. 5,746,855 embodied as an endless strip can be avoided, if the carrier material is cut out, in terms of size and/or shape, in such a way that the cut-out carrier material corresponds to the cross-sectional area of the block. This results in histological sections that adhere to the cut-out carrier material or are mounted thereonto. The cut-out carrier material can be individually delivered, with the histological section mounted thereonto, in automated or manual fashion to a downline processing system, or the microtome operator can individually pick up the cut-out carrier material and the histological section mounted thereonto, for example with a forceps, and apply it onto a specimen slide. In this context, the histological section is applied onto the specimen slide with the surface of the histological section that faces away from the carrier material. The histological section is therefore then located between the carrier material and the specimen slide. It is thus not necessary to handle an endless strip having multiple histological sections applied thereonto, such that in some circumstances certain histological sections become damaged. The histological sections produced in accordance with the method according to the present invention correspondingly do not roll up, and improved downline processing, compared with the procedure using an endless strip as a carrier material, is thus advantageously possible.

According to a preferred embodiment, the carrier material is cut out with the application apparatus. The application apparatus is, accordingly, embodied suitably for cutting out the carrier material before application onto the block. This can be achieved, for example, in that the application apparatus comprises a cutting apparatus. According to this embodiment, therefore, the functions of cutting out and applying the carrier material are combined in the application apparatus. This is discussed in even further detail below.

According to a very particularly preferred embodiment, the carrier material is cut out immediately before the sectioning operation of the histological section. This is a good choice in particular when the carrier material can be cut out with the application apparatus. As a result, the carrier material is cut out, or produced in the appropriate size and/or shape, only when it is actually required. It is thereby possible, for example, to at least largely prevent contamination of the carrier material to be applied onto the block, for example due to the operator's fingerprints.

Very particularly preferably, the cross-sectional area of the cut-out carrier material is somewhat larger than the cross-sectional area of the block. The cross-sectional area of the cut-out carrier material is preferably dimensioned to be up to 10%, in particular approx. 5%, larger than the cross-sectional area of the block. This can be achieved by a corresponding configuration of a cutting tool given predefined dimensions of the block. If the cross-sectional area of the cut-out carrier material is thus configured to be somewhat larger than the cross-sectional area of the block and therefore of the histological section to be produced, an edge region of the carrier material exists, to which region the histological section does not extend. According to this embodiment, the edge region ideally extends entirely around the periphery of the histological section if the carrier material has been applied to the block and the histological section is thus arranged in centered fashion relative to the carrier material.

In a further preferred method step, the histological section that has been produced is transferred, with the applied carrier material, from the blade holder onto a specimen slide and/or is delivered to a downline processing system. This could be accomplished, for example, by the fact that the microtome operator removes the carrier material, with the histological section arranged thereon, using a forceps, and applies it onto a specimen slide or delivers it to another downline processing system. Alternatively thereto, provision could be made for automated transfer of the cut-out carrier material, with the histological section attached thereto, onto a specimen slide, for example using a transport device provided on the blade holder of the microtome and embodied in the form of a transport belt.

Once the histological section, together with the cut-out carrier material, has been applied onto a specimen slide or delivered to a downline processing system, provision is made in a preferred method step to remove or detach the carrier material from the histological section. This could be accomplished, for example, by the action of energy. For example, thermal energy in particular, e.g. of a thermal radiator or of an infrared lamp, could be used to detach the carrier material from the histological section.

Depending on the particular carrier material used, electromagnetic energy of a suitable light source, for example UV light, could also be used to detach the carrier material from the histological section. Alternatively or additionally, the histological section could be detached or removed from the cut-out carrier material by application of a liquid solution. Ultimately, the cut-out carrier material can be removed from the histological section with a specific method step that is suitable with regard to the properties of the carrier material.

According to a very particularly preferred embodiment, the cut-out carrier material is applied onto the block only when the histological section to be produced is to be applied onto a specimen slide and/or is to be delivered to a downline processing system. Accordingly, histological sections that are not be applied onto a specimen slide, or are not to be delivered to a downline processing system, do not have cut-out carrier materials applied onto them. Such histological sections can be, for example, sectioning waste or trimming sections that therefore have a not inconsiderable thickness and are to be produced initially from a block just clamped into the microtome, until the sectioning plane of the block has arrived at a tissue sample of interest. The blocks typically comprise tissue samples that are embedded in paraffin. By means of the paraffin, the blocks are connected to the cassette. The surface of a non-processed block is very rough as long as the block has not yet been cut. A trimming process requiring typically several cuts is necessary for obtaining a smooth surface and making sure the cut penetrates the tissue sample. These trimming cuts cannot be used and are disposed. For these trimming cut, of course no carrier material is applied since the trimming cuts are waste. Avoiding attachment of carrier material can for instance be achieved by stopping the motor, e.g. by simply switching it off.

To those cuts that finally have a smooth surface and penetrate the tissue sample, an apparatus according to the present invention (application apparatus) applies a carrier material onto a histological section to be produced with a microtome. In accordance therewith, a histological section of predefinable thickness is producible, with the microtome, from a block that comprises a tissue sample. Before production of the histological section, a carrier material can be applied with the application apparatus onto the block. According to the present invention, the carrier material can be cut out, before application, to a size and/or a shape that corresponds substantially to the cross-sectional area of the block; and the cut-out carrier material can be applied onto the block.

The apparatus according to the present invention is suitable in particular for carrying out the method according to the invention ; in order to avoid repetition, reference is therefore made to the foregoing portion of the Specification regarding the method features relevant thereto. The apparatus-related features of the method steps that are described or required are apparent, in this context, to a skilled artisan active in the present sector having knowledge of the disclosure of the foregoing portion of the Specification.

Very particularly preferably, the application apparatus comprises a cutting device with which a cut piece of the carrier material can be produced from the uncut carrier material, which piece can be applied onto the block. With the cutting device, therefore, a piece of predefinable size and/or shape is cut to shape or cut out from the uncut carrier material before said piece is applied onto the block.

A dispensing device could furthermore be provided, with which uncut carrier material is deliverable to the cutting device. Alternatively or additionally, a takeup device could be provided, with which the carrier material that is cut and not applied onto the block can be taken up. The provision of a dispensing device and/or a receiving device is useful in particular when the carrier material is embodied in the form of a strip, for example comparably to the strip-shaped carrier material known from U.S. Pat. No. 5,746,855. The dispensing device could receive a roller having strip-shaped carrier material wound on it, which roller can be replaced when the carrier material is consumed. In comparable fashion, the takeup device could comprise a roller onto which the cut material not applied onto the block can be applied.

Concretely, the cutting device could comprise a housing in which a cutting tool for cutting out the carrier material is movably arranged. If blocks having different sizes and/or shapes are to be processed with the microtome, it may be useful for the cutting device to comprise cutting tools of different sizes. Depending on the particular block to be processed, the appropriate cutting tool for cutting out the carrier material is then used.

According to a preferred embodiment, the carrier material to be cut out is guidable between the housing of the cutting device and a countermember. Suitable guidance means could be provided for this, for example guide rollers, with which the carrier material is guided in a predefinable direction. The countermember can be, for example, a plate or a plate-shaped component that comes into engagement with the cutting tools when the carrier material is cut out. The plate-shaped component could have an opening that corresponds substantially to the size and/or shape of the cut piece, so that after production of the cut piece, the cut-out carrier material can be transferred through the countermember and applied onto the block.

Concretely, the carrier material could be capable of being cut out by the fact that the cutting tool is movable in the direction of the countermember. This could be brought about, in particular, by the fact that the cutting tool is moved sufficiently far that it can be brought into contact with the countermember. If the countermember then has an opening, the cutting tool could be moved toward the countermember and past a portion of the countermember. In this case the shape of the portion of the cutting tool provided for cutting would need to be configured in a fashion substantially complementary to the opening of the countermember, so that the cutting tool can be moved partly through the opening and the carrier material is thereby cut out.

According to a preferred embodiment, the cutting device comprises a contact pressure element with which the cut-out carrier material can be moved or applied onto the block. Provision could be made, in particular, that the contact pressure element can be pressed with a predefinable pressure onto the block so as thereby to press the cut-out carrier material with the predefinable pressure onto the block, and thus apply the cut-out carrier material in substantially uniform fashion onto the block, and/or to ensure secure contact between the cut-out carrier material and the histological section.

To allow automation of the application operation, the cutting device, dispensing device, takeup device, and/or cutting tool can preferably be driven or moved in motorized fashion. At least one drive motor could be provided for this purpose, for example embodied in the form of a stepping motor or a DC motor. If the carrier material is delivered or discharged manually, and only the cutting tool of the cutting device is embodied in motorized fashion, only one drive motor or electric motor is required. If the carrier material is additionally delivered or discharged in motorized fashion, a further drive motor could be provided on the takeup device, which motor moves the carrier material from the dispensing device past the cutting device to the takeup device, or pulls it to the takeup device.

The microtome could be a rotary microtome, a sliding microtome, or a rotating disc microtome. The apparatus according to the present invention is preferably provided for a rotary microtome, although it is also usable with the other types of microtome. With a rotary microtome, the block that comprises at least one tissue sample is mounted on a cassette associated with the block. The cassette is clamped in a specimen holder of the microtome. The cassette together with the block is moved upward and downward, using the specimen holder, substantially in a vertical direction, and in that context moved (advanced) substantially in a horizontal direction, a predefinable distance toward the blade that is arranged in stationary fashion, thereby producing histological sections of a predefinable thickness that corresponds to the prefinable distance of the horizontal advance motion of the specimen holder. With a rotary microtome, the apparatus according to the present invention is to be arranged between the microtome operator and the block surface that is to be sectioned. This can, however, complicate access to the specimen holder and/or the blade holder of the microtome, and to the operating elements therefor. According to a preferred embodiment, a motion device is therefore provided with which the apparatus is transferable from a position spaced away from the block into a position in proximity to the block. With the motion device, the apparatus could therefore be moved a short distance (for example, a few centimeters) in a direction toward the block or away from it. Provision could be made, however, that with the motion device the apparatus can be transferred from a position from which the cut-out carrier material can be applied onto the block into a position in which the apparatus is movable largely out of the region in which the operator accesses the operating elements of the blade holder and/or of the specimen holder, for example to one side, upward, or downward. In this case the motion to be performed by the apparatus can be complex.

With a rotary microtome, for production of a histological section the block is transferred in a vertical direction from an upper position into a lower position. The surface of the block is thereby moved past the blade. The histological section is thereby produced. It may therefore be useful if the apparatus according to the present invention for application of a carrier material is arranged on the block, relative to the microtome, in such a way that the application apparatus is arranged in a position that is located substantially opposite the surface of the block in the upper vertical position of the block. The carrier material to be cut out can then accordingly be applied, using the application apparatus, onto the block when the latter is still in the upper position before production of the histological section.

The histological sample or tissue sample is preferably embedded in an embedding medium. A block is thereby formed. The cross section of the block is round and, in particular, of circular configuration. In other words the block, in the context of a circular cross section, preferably has a cylindrical or a truncated conical shape. The cross section or shape of a histological section from such a block is accordingly round or circular. Because of the round or circular cross sections, multiple such histological sections produced in succession, when they form a section strip, are therefore connected to one another only at connecting points that extend over a smaller region (ideally, for example, only at one contact point) than is the case for histological sections of rectangular cross section (in which the connecting point of two histological sections extends over an entire adjacent side surface). A section strip made up of histological sections having a round or circular cross section can therefore be split up more easily. This is also the case when the histological sections are each equipped with cut-out carrier material.

If the cross section of the block is rectangular or round, provision is then preferably made that the cross section of the carrier material to be applied onto the block is likewise embodied in rectangular or round, and in particularly circular, fashion. It is also conceivable in the context of a rectangular block cross section, however, to cut out and apply onto the block a respective carrier material that has a round or circular cross section. In this case the size of the cut-out carrier material is preferably selected in such a way that the entire histological section to be produced is covered with the carrier material. In other words, the diameter of the circular cross section of the carrier material is larger than the side lengths of the rectangular cross section of the block. The converse case is likewise conceivable. In this context the cross section of the block is round or circular. The cross section of the carrier material to be cut out could in this case be embodied in rectangular or square fashion, preferably in such a way that the entire histological section is covered with carrier material.

The carrier material is preferably embodied in the form of a strip. This makes possible simple handling of the carrier material, as was indicated in connection with the dispensing device and the takeup device.

To ensure that the histological section, with the cut-out carrier material mounted thereon, can easily be applied onto a specimen slide, according to a preferred embodiment an opening for reception of the specimen slide is provided on the blade holder, preferably not far away from the blade. The surface of the specimen slide received in the opening is substantially flush with the surface of the blade holder, at least on a side facing toward the blade. The histological section that has been produced is movable in the context of the sectioning operation at least partly onto the specimen slide received in the opening. With this feature, the histological section that has been produced, onto which the cut-out carrier material is applied, can be applied or slid, in almost automatic fashion along with the sectioning operation, onto the specimen slide. If applicable, the specimen slide can have a coating such that the histological section can be slid with as little friction as possible onto the specimen slide.

Very particularly preferably, the apparatus according to the present invention is provided on a microtome for producing histological sections.

There are various ways of advantageously embodying and refining the teaching of the present invention. In the following, the invention is explained in more detail by preferred exemplifying embodiments of the invention with reference to the drawings. In conjunction with the explanation of the preferred exemplifying embodiments of the invention with reference to the drawings, an explanation is also given of generally preferred embodiments and refinements of the teaching.

BRIEF DESCRIPTION OF THE DRAWINGS

In the drawings, in schematically depicted fashion in each case:

FIGS. 3 to 6 are each sectioned views of the exemplifying embodiment according to FIG. 1, each showing a different operating state of the cutting tool;

FIGS. 3a to 6a are smaller side views of the exemplifying embodiment according to FIGS. 3 to 6, respectively;

FIG. 7a is a sectioned view of a histological section, applied onto a specimen slide, onto which a cut-out carrier material has been applied; and FIG. 7b is a plan view of a specimen slide, the histological section, and the cut-out carrier material of FIG. 7a.

DETAILED DESCRIPTION OF THE DRAWINGS

Figure 1:
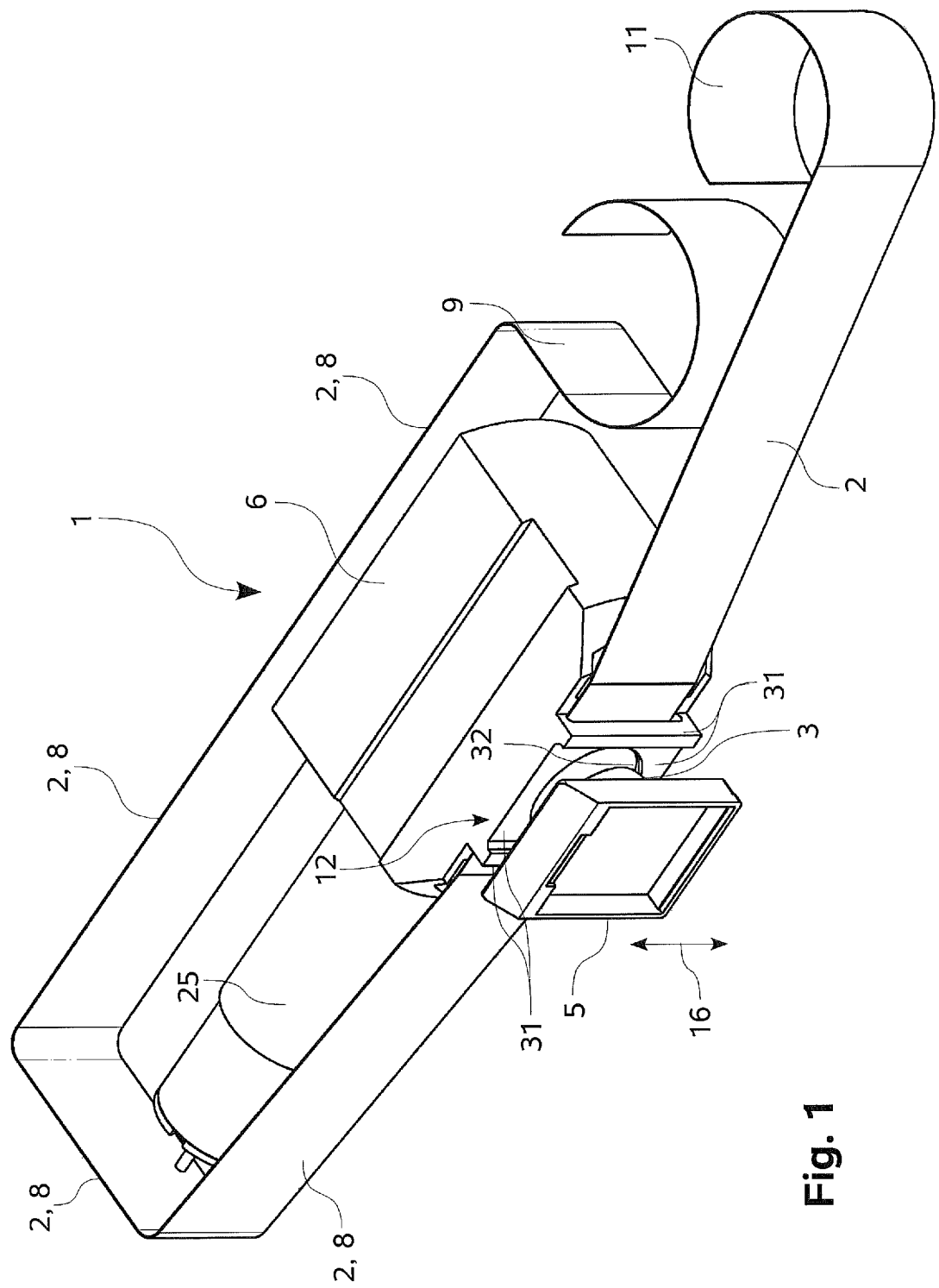
FIG. 1 is a perspective view of an exemplifying embodiment of an apparatus according to the present invention with a carrier material that has not been cut.

In the Figures, identical or similar components are labeled with the same reference characters. FIGS. 1 to 6 show apparatus 1 according to the present invention for applying a carrier material 2 onto a histological section to be produced with a microtome. The microtome is not shown in the Figures. The histological section is produced from a block 3 in which a histological sample or tissue sample 4 is embedded in an embedding medium (see e.g. FIG. 3 or 3a). The cross section of block 3 is round, and in particular of circular configuration. For example, it is evident from FIG. 3a that block 3 has a truncated conical shape. Block 3 is mounted on cassette 5, cassette 5 being clamped into the specimen holder of the microtome. An application apparatus 6 is provided with which, prior to production of the histological section, a carrier material 2 can be applied onto block 3. According to the present invention carrier material 2 can be cut out, prior to application onto block 3, to a size and a shape that correspond substantially to the cross-sectional area of block 3. Only the cut-out carrier material is applied onto block 3.

Apparatus 1 is suitable for a rotary microtome. Apparatus 1 is arranged relative to the microtome in such a way that application apparatus 6 is arranged at a position that is located substantially opposite surface 7 of block 3 in the upper vertical position of the block's motion in the context of the production of histological sections with the rotary microtome. This state is indicated in FIGS. 1 and 2, and 3a to 6a. The cut-out carrier material can accordingly be applied onto surface 7 of block 3, using application apparatus 6, when block 3 is still in the upper position before production of the histological section. Block 3 and cassette 5 are moved by the rotary microtome vertically upward and downward along the direction of double arrow 16.

Figure 2:
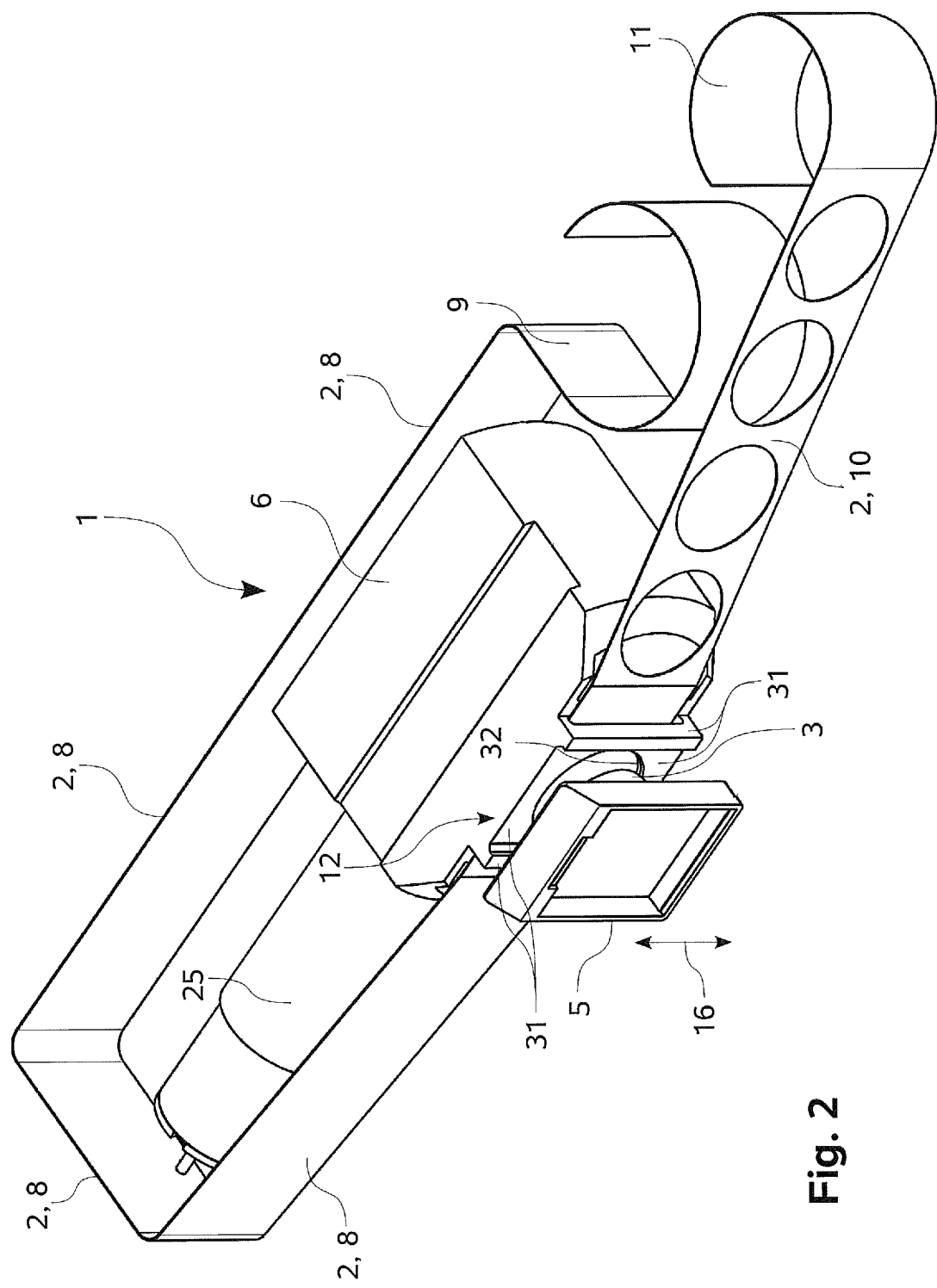
FIG. 2 is a perspective view of the exemplifying embodiment according to FIG. 1, in which multiple cut-out carrier materials have been produced from the carrier material.

Carrier material 2 is embodied in the form of a strip. A dispensing device indicated with the reference character 9 is provided for the uncut carrier material 2, 8. Dispensing device 9 comprises a roller (not shown) on which the uncut carrier material 8 is wound. A takeup device indicated with the reference character 11 is provided for carrier material 2, 10 that is cut and not applied onto the block. Takeup device 11 likewise comprises a roller (not shown) onto which the carrier material 10 that is cut and not applied onto the block can be wound and thereby taken up. This is shown in FIG. 2. FIG. 1, on the other hand, shows apparatus 1, with applied carrier material 2, in a state in which no cut-out carrier materials have yet been applied onto a block 3. Apparatus 1 is in the state shown in FIG. 1, for example, when a new carrier material 2 is clamped in place. Carrier material 2 is thus guided by dispensing device 9 around the entire apparatus 1 to takeup device 11, not all of the guide elements necessary for this being shown in the Figures.

Application apparatus 6 encompasses a cutting device 12 with which a cut piece of carrier material 2 can be produced from the uncut carrier material 2, 8, which piece can be applied onto block 3. The cutting out of carrier material 8 using application apparatus 6 accordingly takes place immediately before the histological section sectioning operation. Cutting device 12 is shown in FIGS. 3 to 6 in a sectioned view. Cutting device 12 encompasses a housing 13 in which a cutting tool 14 for cutting out carrier material 2 is movably arranged. The cutting tool 14 or punch is embodied in the shape of a cylinder or piston, and can be moved in housing 13 along the direction of motion indicated with double arrow 15. A guide pin 17 is mounted on cutting tool 14, which pin is guided, at the end facing away from cutting tool 14, in an opening 18 in housing 13. As a result, on the one hand an end stop can be constituted for cutting tool 14 (cf. FIG. 6), and on the other hand rotation of cutting tool 14 about its longitudinal axis in housing 13 can be prevented. The present position of cutting tool 14 in housing 13 can be determined with sensor 19. Cutting tool 14 comprises an orifice 20 in the form of a blind hole, in which spring 21 preloads contact pressure element 22. Contact pressure element 22 has an opening or elongated hole 23 through which pin 24 extends, in the orifices provided therefor in cutting tool 14, through contact pressure element 22. Pin 24 can prevent contact pressure element 22 from falling out of orifice 20 (see e.g. FIG. 3). As a result of elongated hole 23, however, contact pressure element 22 can penetrate into cutting tool 14 against the spring force of spring 21 (see FIG. 6).

The motion of cutting tool 14 in housing 13 is driven by drive motor 25, embodied in the form of a DC motor. Drive 25, with its output shaft 26, imparts a rotation to wheel 27. A pin 28 is arranged eccentrically on wheel 27. Wheel 29 is mounted rotatably on pin 28. Wheel 29 can move, in opening 30 provided in cutting tool 14, in a direction perpendicular to the drawing plane. As a result of the rotation of wheel 27 and thus the eccentric motion of wheel 29, the cutting tool (driven by drive motor 25) is moved in the direction of double arrow 15, specifically from a position shown in FIG. 3 through the positions shown respectively in FIGS. 4 and 5 to a position shown in FIG. 6.

Carrier material 8 to be cut out is guidable between housing 13 of cutting device 12 and a countermember 31. Countermember 31 is embodied in substantially plate-shaped fashion and has a circular hole 32. The plate-shaped part of countermember 31 is at distance d from housing 13. The diameter of hole 32 corresponds to the diameter of orifice 33 in housing 13, in which orifice cutting tool 14 is guided. Cutting tool 14 can accordingly be moved, with the end facing toward block 3, through hole 32 of countermember 31, as shown in FIGS. 5 and 6.

Carrier material 8 can be cut out by the fact that cutting tool 14 is movable in the direction of countermember 31. For this, cutting tool 14 is firstly brought into contact with the plate-shaped part of countermember 31 (see FIG. 4). The annularly shaped end 37 of cutting tool 14 is then moved past the plate-shaped part of countermember 31 (see FIGS. 5 and 6). The result is on the one hand that a circular cut piece is produced from carrier 8. On the other hand, the motion of cutting tool 14 toward block 3 causes the cut-out carrier material to be applied onto the surface of block 3. The application operation is assisted by contact pressure element 22, which has a circular surface of planar configuration facing toward block 3, on which surface the circular cut piece of carrier material is moved to block 3. Because of the spring preload of spring 21, the cut-out carrier material can be pressed onto block 3 (see FIG. 6). The spring constant of spring 21 is selected appropriately for this.

The roller of takeup device 11 can likewise be moved in motorized fashion so that as a result, uncut carrier material 8 can be transported from dispensing device 9 to cutting device 12. The drive motor provided for this is not shown in the Figures.

FIGS. 3a to 6a each show, in a smaller side view, the exemplifying embodiment in accordance with the respective FIGS. 3 to 6, the respective position of cutting tool 14 and, in particular, of annular end 37 of cutting tool 14 being evident and indicated in the respective FIGS. 3a to 6a.

The method according to the present invention for producing histological sections with a microtome can be carried out with apparatus 1 according to the present invention shown in the Figures. FIGS. 7a and 7b indicate, in merely schematic fashion, that the histological section 34 that has been produced is transferred, with carrier material 35 applied thereonto, onto a specimen slide 36 and can thus be delivered to a downline processing system. Histological section 34 is thus arranged between specimen slide 36 and the cut-out carrier material 35. The cut-out carrier material 35 is, however, applied onto block 3 only when histological section 34 that is to be produced is intended to be applied onto a specimen slide 36. The cross-sectional area of the cut-out carrier material 35 is somewhat larger than the cross-sectional area of block 3, and thus of histological section 34 resulting therefrom. Concretely, the diameter of the cut-out carrier material 35 corresponds to the diameter of hole 32 in countermember 31, or to the diameter of cutting tool 14. The diameter of the cut-out carrier material 35 is larger than the diameter of histological section 34, so that the outer edge region of carrier material 35 can be gripped, for example, with a forceps without damage to histological section 34 by the forceps.

In conclusion, be it noted very particularly that the exemplifying embodiments discussed above serve merely to describe the teaching claimed, but do not limit it to the exemplifying embodiments.

LIST OF REFERENCE NUMERALS

1 Apparatus for applying carrier material onto histological sections
2 Carrier material
3 Block
4 Tissue sample
5 Cassette
6 Application apparatus
7 Surface of block 3
8 Uncut carrier material
9 Dispensing device
10 Cut carrier material
11 Takeup device
12 Cutting device
13 Housing of the cutting device 12
14 Cutting tool
15 Direction of motion of the cutting tool 14
16 Direction of motion of the block 3 and the cassette 5
17 Guide pin
18 Opening in the housing 13 for the guide pin 17
19 Sensor
20 Orifice
21 Spring
22 Contact pressure element
23 Elongated hole of the contact pressure element 22
24 Pin
25 Drive motor
26 Output shaft of drive motor 25
27 Wheel
28 Pin
29 Wheel mounted rotatably on pin 28
30 Opening in the cutting tool 14 in which the wheel 29 can move
31 Countermember
32 Hole in the countermember 31
33 Orifice in the housing 13 in which the cutting tool 14 is guided
34 Histological section
35 Cut-out carrier material applied onto the histological section 34
36 Specimen slide
37 Annular end of the cutting tool 14
d Distance from plate-shaped part of the countermember 31 to the housing 13

The invention claimed is:

1. A method for producing individual and separated histological sections that adhere to respective individual and separated pieces of a carrier material by means of a microtome from a block comprising a paraffin embedded tissue sample, comprising the following method steps in the sequential order a) to d) in an automated process:
   a) automatically cutting out immediately prior to cutting the histological section a piece of the carrier material by means of an application apparatus located substantially opposite to the block, further comprising a cutting device that cuts the uncut carrier material according to at least one of a size and a shape corresponding substantially to a cross-sectional area of the block; wherein the cutting device further comprises a housing in which a cutting tool for cutting out carrier material is movably arranged;
   b) automatically applying the piece of carrier material by means of the application apparatus onto the block so that the piece of the carrier material adheres to the block, wherein cutting out the piece of the carrier material and applying the cut out piece of the carrier material to the block is performed in one continuous motion performed by the application apparatus using a drive motor in the application apparatus;
   c) producing the histological section by cutting the block underneath the piece of carrier material adhering to the block; and
   d) transferring the produced histological section with the applied carrier material from a blade holder of the microtome to at least one of a specimen slide and a down line processing system.

2. The method according to claim 1, further comprising of providing that the cross-sectional area of the cut-out carrier material is between 5 and 10% larger than the cross-sectional area of the block.

3. The method according to claim 1, further comprising of detaching the carrier material from the histological section by one of applying thermal energy, electromagnetic energy and a liquid solution.

4. An apparatus for applying a carrier material onto a histological section to be produced by means of a microtome, said histological section having a predefined thickness and being cut out from a block that comprises a tissue sample, said apparatus comprising:
- a guide that guides the carrier material to be cut out between the housing of a cutting device and a counter member;
- the cutting device for cutting out a larger piece of the carrier material from a larger part of uncut carrier material prior to application of the carrier material according to at least one of the size and shape corresponding substantially to the cross-sectional area of the block, wherein the cutting device comprises a housing in which a cutting tool is movable in the direction of the counter member for cutting out the piece of the carrier material, and the cutting device comprises a contact pressure element by which the cut-out carrier material can be moved to and applied onto the block; and
- a drive motor moving the cutting device from a position spaced away from the block into a position in proximity to the block, said drive motor and cutting device being configured to cutting out the piece of the carrier material and applying the cut out piece of the carrier material to the block in one continuous motion.

5. The apparatus according to claim 4, further comprising a dispensing device delivering the uncut carrier material to the cutting device.

6. The apparatus according to claim 4, further comprising a takeup device configured to take up the piece of the carrier material that is cut and not applied onto the block.

7. The apparatus according to claim 4, wherein the cutting device is designed such that a cutting action is completed when the cutting tool is brought into contact with the counter member.

8. The apparatus according to claim 4, wherein the cutting device is designed such that a cutting action is completed when the cutting tool is moved past a portion of the counter member.

9. The apparatus according to claim 4, wherein the contact pressure element is configured to press the cut-out carrier material with a predefinable pressure onto the block.

10. The apparatus according to claim 4, wherein the histological sample is embedded in an embedding medium and the block is thereby formed; and the cross section of the block has one of the shapes rectangular, rounded and circular.

11. The apparatus according to claim 4, wherein the cross section of the carrier material to be applied onto the block has one of the shapes rectangular, rounded and circular.

12. The apparatus according to claim 4, wherein the carrier material has the shape of a strip.

13. The apparatus according to claim 4, wherein an opening for receiving a specimen slide is provided on the blade holder; the surface of the specimen slide received in the opening is at least on a side facing toward the blade substantially flush with the surface of the blade holder; and the histological section that has been produced is movable during cutting action at least partly onto the specimen slide received in the opening.

* * * * *